United States Patent [19]
Kanesaka et al.

[11] Patent Number: 6,129,754
[45] Date of Patent: Oct. 10, 2000

[54] STENT FOR VESSEL WITH BRANCH

[75] Inventors: Nozomu Kanesaka; George A. Tashji, both of Hillsdale, N.J.

[73] Assignee: Uni-Cath Inc., Saddle Brook, N.J.

[21] Appl. No.: 08/988,442

[22] Filed: Dec. 11, 1997

[51] Int. Cl.$^7$ ........................................... A61F 2/06
[52] U.S. Cl. .............................. 623/1; 623/12; 606/153; 606/191; 606/195; 606/198
[58] Field of Search ................... 623/1, 12; 606/153, 606/191, 195, 198

[56] References Cited

U.S. PATENT DOCUMENTS

| | | | |
|---|---|---|---|
| 5,104,404 | 4/1992 | Wolff | 623/1 |
| 5,449,373 | 9/1995 | Pinchasik et al. | 623/1 |
| 5,591,197 | 1/1997 | Orth et al. | 623/1 |
| 5,697,971 | 12/1997 | Fischell et al. | 623/1 |
| 5,733,303 | 3/1998 | Israel et al. | 623/12 |
| 5,755,781 | 5/1998 | Jayaraman | 623/1 |
| 5,776,183 | 7/1998 | Kanesaka et al. | 623/12 |
| 5,824,040 | 10/1998 | Cox et al. | 623/1 |
| 5,824,045 | 10/1998 | Alt | 623/12 |

*Primary Examiner*—Paul B. Prebilic
*Attorney, Agent, or Firm*—Kanesaka & Takeuchi

[57] ABSTRACT

An expandable reinforcing member or stent of the invention is used inside a body lumen, especially, in patient's artery for opening and holding a lesion or stenosis with a branch. The expandable reinforcing member is formed of at least two hollow mesh portions situated away from each other along an axial direction of the reinforcing member, and a connecting portion situated between the two hollow mesh porions for connecting the same. The connecting portion has a plurality of tortuous lines to define hollow areas therein, and a marker. Each hollow area is greater than a mesh size of the hollow mesh portions, and the marker is formed in one of the tortuous lines. Thus, a position of the connecting portion is realized at a time of installation of the reinforcing member. After the expandable reinforcing member is expanded, the reinforcing member can be slightly moved to relocate the position.

5 Claims, 2 Drawing Sheets

STENT FOR VESSEL WITH BRANCH

BACKGROUND OF THE INVENTION AND RELATED ART STATEMENT

The present invention relates to an expandable reinforcing member or stent suitable for a vessel with a branch.

"Stent", which is defined here as a prosthetic member used for reinforcing the blood vessel, has been used in the interluminal vascular treatment in place of surgical exposing, incising, removing, replacing or bypassing a defected portion of a blood vessel required in the conventional vascular surgery.

The stent generally has a tubular shape and functions to support a part of a blood vessel or other anatomical lumen from the inside thereof, and is particularly suitable for supporting and holding a dissected arterial lining which may occlude a fluid passageway by collapse thereof.

There are many types of stents, such as tubular stent formed of a tubular metal plate with holes therein by cutting or etching, wire stent formed of a flat or round wire and arranged in a cylindrical shape, self expanding stent, and balloon expanding stent, and so on.

In view of the reason that the stent is placed in a patient's body cavity, i.e. blood vessel, to support a cavity wall, generally speaking, the tubular stent with the holes therein is better than the wire stent, because the tubular stent can withstand a high radial force to support the cavity wall. However, since a wire stent can be relatively easily moved and/or deformed after installation in the blood vessel, it is convenient to use the wire stent for the blood vessel with a branch. Namely, if a wire segment of the wire stent blocks a branch hole of a blood vessel when the wire stent is installed by a balloon catheter, the wire stent can be slightly moved further by the balloon catheter not to block the hole of the branch.

In this respect, since the outer surfaces of the tubular stent is not so smooth, after the stent is expanded and installed in the blood vessel, it is difficult to move the stent. Also, it is difficult to dispose the tubular stent without blocking the branch hole. Thus, it is better not to use the conventional tubular stent when the blood vessel with the branch portion is to be supported.

On the other hand, when the stent is installed into the blood vessel, the stent in a closed condition is mounted on a catheter, e.g. balloon catheter, and delivered to the lesion or stenosis by the balloon catheter. Since the stent in the closed condition is not flexible in the longitudinal direction thereof, if the stent is long, it is difficult to deliver the stent through a meandering artery in and around the calcified lesion without damaging the blood vessel.

In this respect, if the diameter of the stent in the closed condition is small, it is easy to pass the narrow and meandering artery. However, the small diameter stent can not be expanded too large, because when the stent is expanded widely, the stent can not sufficiently support. Namely, in order to sufficiently support the artery, the stent must have a large number of supports, so that the stent can not be expanded to have a large diameter. Otherwise, the stent must have a large diameter.

Accordingly, one object of the invention is to provide a stent, which provides a support on a main vessel and a large opening for a side branch.

Another object of the invention is to provide a stent as stated above, wherein the stent can be slightly moved and/or deformed easily after installation if required.

A further object of the invention is to provide a stent as stated above, which can be easily delivered through the meandering and narrow artery without damaging the vessel.

Further objects and advantages of the invention will be apparent from the following description of the invention.

SUMMARY OF THE INVENTION

A stent or expandable reinforcing member of the invention is formed of at least two hollow mesh portions situated away from each other along an axial direction of the stent, and a connecting portion situated between the two hollow mesh portions for connecting the same. The connecting portion has a plurality of tortuous lines to define hollow areas or spaces therein, and a marker formed in one of the tortuous lines. In the connecting portion, few numbers of the tortuous lines are formed so that the tortuous lines can be moved or deformed. The hollow area may have a size greater than a mesh size formed in the hollow mesh portions. The marker is formed so that a position of the connecting portion is realized at a time of installation of the reinforcing member by, e.g. fluoroscopy.

The reinforcing member of the invention is useful for supporting a vessel with a branch, or artery. The connecting portion is located at a branch hole of the vessel, and the two hollow mesh portions support both sides of the branch hole. Since the connecting portion has the hollow areas, each being greater than a size of a hole forming a part of the hollow mesh portion, the connecting portion does not block fluid or blood passage through the branch hole. Also, if necessary, the reinforcing member can be easily moved to properly locate the connecting portion relative to the branch hole.

When the reinforcing member or stent of the invention is used, the reinforcing member is disposed over a balloon catheter and is delivered to a desired portion inside the vessel or blood vessel. Then, the reinforcing member is expanded by the balloon catheter. As a result, the hollow mesh portions and the connecting portion are substantially equally expanded. The diameter of the reinforcing member in the expanded state is substantially the same throughout the entire length thereof.

In the invention, the connecting portion is located at the branch hole. In this respect, since the marker is formed in the connecting portion, the location of the connecting portion can be easily checked. After the reinforcing member is expanded, if it is necessary to move the reinforcing member, the balloon catheter is once again located inside the reinforcing member and is inflated to hold the reinforcing member. Then, the balloon catheter is manipulated to move or deform the reinforcing member. Since the connecting portion has the large hollow areas, the reinforcing member can be moved relatively easily in the vessel.

Each hollow mesh portion is formed of a plurality of rows of circularly arranged joint members, and a plurality of rows of circularly arranged elongated members situated between adjacent two rows of the joint members. Each row is arranged circularly around a central axis of the reinforcing member and is connected along a direction of the central axis.

The elongated members in each row are inclined substantially in a same direction and diagonally with an acute angle with respect to a line on a surface of the reinforcing member parallel to the central axis of the reinforcing member. Each elongated member connects two of the joint members situated in adjacent two rows of the joint members. The elongated members in two rows sandwich one row of the joint members to be arranged substantially symmetrically relative to one row of the joint members. When a radial force is applied from an inside of the reinforcing member, the elongated members are pivoted relative to the joint members to thereby allow the reinforcing member to have a second diameter larger than a first diameter.

Each hollow mesh portion further includes an end section having second elongated members arranged parallel to the central axis of the reinforcing member and connected to the circularly arranged joint members, and end bars. Each end bar connects two adjacent second elongated members.

DETAILED DESCRIPTION OF PREFERRED EMBODIMENTS

Figure 1:
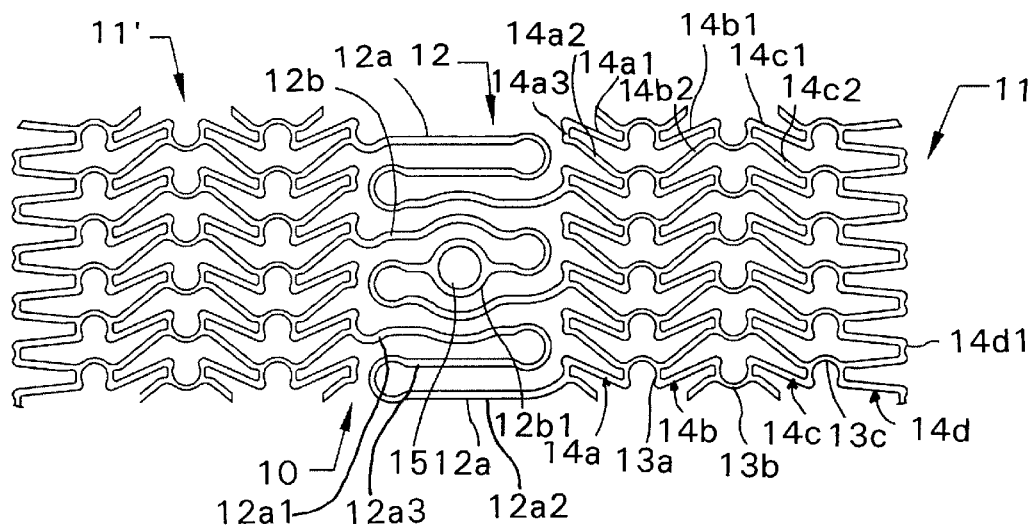
FIG. 1 is an explanatory plan view of a stent in a flat sheet form according to the present invention.
Figure 2:
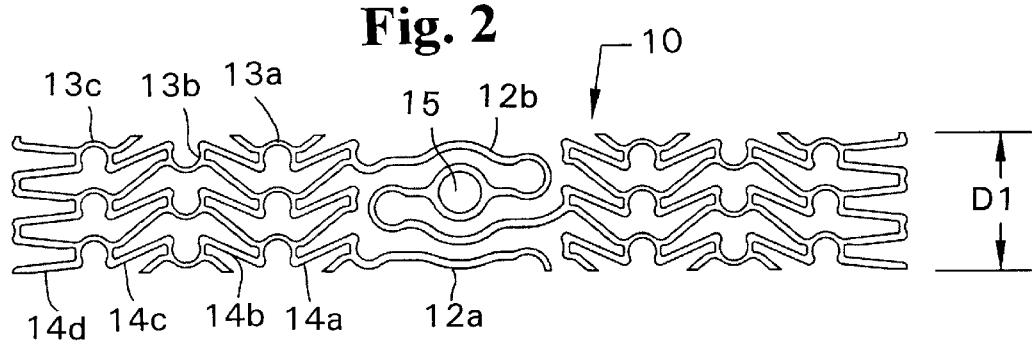
FIG. 2 is an explanatory side view of the stent in a circular form.
Figure 3:
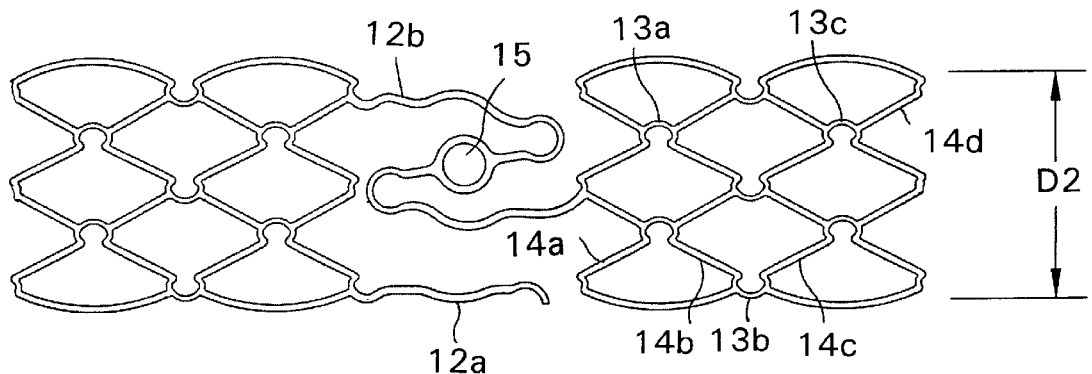
FIG. 3 is an explanatory side view of the stent in an expanded condition.
Figure 4:
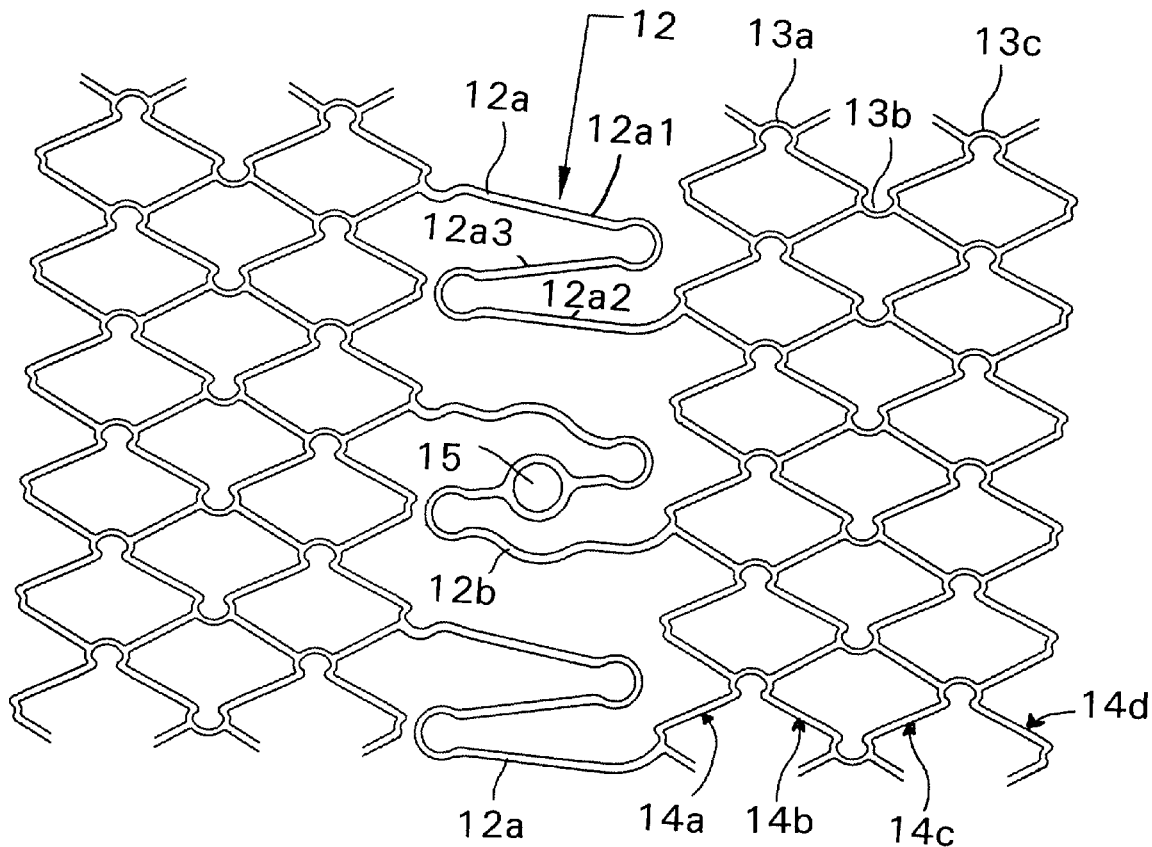
FIG. 4 is an explanatory plan view of the stent in a flat sheet form in an expanded condition.

A stent or reinforcing member 10 of the present invention is explained with reference to the drawings.

The stent 10 is basically formed of two mesh portions 11, 11' and a connecting portion 12 situated between the mesh portions 11, 11'. The two mesh portions 11, 11' have the same structures, and are arranged symmetrically relative to the connecting portion 12. For explanation, the mesh portion 11 is only explained hereunder.

The mesh portion 11 includes three rows of joint members 13a, 13b, 13c, and four rows of elongated members 14a, 14b, 14c, 14d, which are arranged circularly relative to the central axis of the stent 10. The joint members 13a, 13b, 13c have a C-shape, and are spaced apart from each other in each row. The joint members 13a, 13c in the drawings have open sides facing downwardly, while the joint members 13b have open sides facing upwardly.

The elongated members 14a include two kinds of members 14a1, 14a2, which incline substantially in the same directions but not parallel to each other, and end bars 14a3 for connecting two of the members 14a1, 14a2. Also, the members 14a1, 14a2 are connected to the joint members 13a.

The elongated members 14b include two kinds of members 14b1, 14b2, which are disposed between the joint members 13a, 13b. The elongated members 14c include two kinds of members 14c1, 14c2, which are disposed between the joint members 13b, 13c.

The elongated members 14a, 14c incline in the same direction, while the elongated members 14b incline in the opposite direction. The elongated members 14a, 14b are arranged symmetrically relative to the joint members 13a, while the elongated members 14b, 14c are arranged symmetrically relative to the joint members 13b. Four elongated members with joint members (end bar) form one opening in the mesh portions 11'.

The elongated members 14d are arranged substantially parallel to the central axis of the stent 10, and two of the elongated members 14d are connected by an end bar 14d1, respectively.

The connecting portion 12 has three tortuous lines 12a, 12b for connecting the mesh portions 11, 11', which extends back and fourth two times to have three sections, i.e. end sections 12a1, 12a2 and center section 12a3, to cover a wide area without forming a mesh therein. The tortuous line 12b includes a circular portion 12b1 in a center thereof, wherein a marker 15 is disposed. The marker 15 may be made of gold or tantalum, so that when the stent 10 is implanted in the body, the location of the marker 15 can be recognized easily by X-ray, fluoroscopy and so on.

Figure 5:
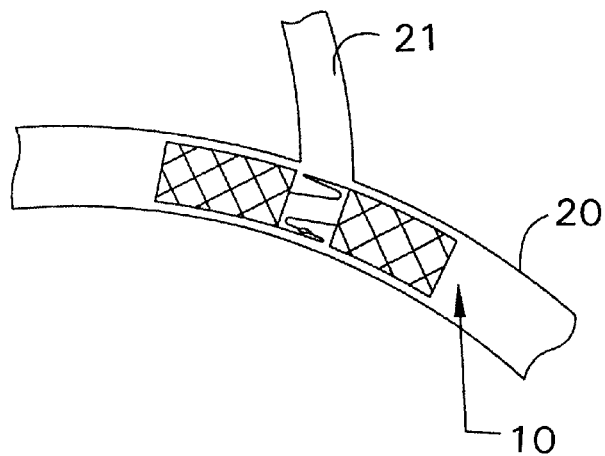
FIG. 5 is an explanatory perspective view for showing the stent disposed in a blood vessel.

As shown in FIG. 5, the stent 10 of the invention is designed for supporting an artery 20 with a branch 21. The connecting portion 12 is located around the branch hole not to block a blood flow through the branch hole, while the mesh portions 11, 11' are located on both sides of the branch hole to support the artery 20.

When the stent 10 is delivered to the artery 20 with the branch 21, a balloon section of a balloon catheter, which is already known in the art, is inserted into a center of the stent 10 to securely hold the stent 10. At this time, the stent 10 has the diameter D1 as it is made. Then, the stent 10 mounted on the balloon catheter is delivered through the meandering narrow body lumen or artery. When the stent 10 is located in the branch 21, the stent 10 is expanded by the balloon to have the diameter D2. Thus, the stent 10 has substantially the same diameter throughout the entire length thereof. Thereafter, the balloon is deflated, and is removed from the artery 20.

In the invention, since the marker 15 is situated in the connecting portion 12, when the stent 10 is located in the artery 20, the connecting portion 12 can be located around the branch hole. However, when the stent is expanded, the stent may be slightly moved, so that the branch hole may not be properly located in the connecting portion, which blocks a blood flow through the branch 21.

In the invention, if it is confirmed by the marker 15 that the stent 10 is not properly located, a balloon is once again delivered inside the stent 10. After the balloon is inflated, the catheter is moved to relocate the stent 10. In the invention, since the connecting portion 12 does not have the mesh therein, the stent 10 can be easily relocated if necessary. Since the connecting portion 12 has the tortuous lines, a part of the artery can still be supported by the tortuous lines. Further, since the mesh portions 11, 11' are formed on both sides of the connecting portion 12, the required portions of the artery can be properly supported by the mesh portions 11, 11'.

In the invention, the mesh portions 11, 11' are formed of the joint members and the elongated members alternately arranged to each other, and the elongated members incline on the surface of the stent relative to the line parallel to the central axis of the stent. Therefore, when the balloon is inflated, the mesh portion 11, 11' can be expanded relatively easily. Also, the expanded mesh portion 11, 11' can withstand the strong radial force applied thereto. The mesh portions 11, 11' operate substantially the same as disclosed in U.S. patent application Ser. No. 08/702,167 filed on Aug. 23, 1996. The content of the application Ser. No. 08/702,167 is incorporated herein.

In the invention, since the mesh portions 11, 11' are connected by the connecting portion 12, the stent 10 is made relatively flexible in the axial direction, because the stent can bend at the connecting portion 12. Therefore, when the stent 10 is delivered in the artery, the stent 10 can slightly bend according to the shape of the artery. Therefore, the stent 10 does not hurt the artery when it is delivered.

In the invention, the mesh size, length and diameter of the mesh portions 11, 11' and the connecting portion 12 may be selected as desired. Although in the embodiment of the invention, a mesh pattern is constant throughout the entire length of the mesh portion, the mesh pattern may be changed as desired.

In the invention, the stent may be coated with medication anti-coagulant, such as heparin. Also, the stent may be coated with polymer so that blood is not easily coagulated. Preferably, the stent is coated with polymer impregnated with medication. Further, the stent may be made of metal with a spring ability or memory expanding metal for self expansion.

While the invention has been explained with reference to the specific embodiments of the invention, the explanation is illustrative and the invention is limited only by the appended claims.

What is claimed is:

1. An expandable reinforcing member, comprising:

at least two cylindrical hollow mesh portions situated away from each other along an axial direction of the reinforcing member, each hollow mesh portion having a plurality of openings arranged circularly in the hollow mesh portion, a connecting portion situated between the two hollow mesh portions for connecting the same, said connecting portion having a plurality of tortuous lines to define hollow areas therein, each hollow area being surrounded by two of the tortuous lines and edges of the hollow mesh portions, a number of the tortuous lines in the connecting portion being less than that of the openings circularly arranged in the hollow mesh portion adjacent the connecting portion, each of the tortuous lines having end sections connected to the respective hollow mesh portions and a center section between the end sections so that said end sections and center section, in a non-expanded condition of the reinforcing member, extend substantially along a central axis of the reinforcing member, and said center section, in an expanded condition, is oriented obliquely relative to the end sections while the end sections extend substantially along the central axis in the expanded condition, and a marker formed in one of the tortuous lines and located in a middle thereof between the two hollow mesh portions so that a position of the connecting portion is identified at a time of installation of the reinforcing member.

2. An expandable reinforcing member according to claim 1, wherein each of said hollow areas is greater in size than each of the openings in the hollow mesh portions in the expanded condition.

3. An expandable reinforcing member according to claim 1, wherein each hollow mesh portion is formed of a plurality of rows of joint members, said each row being arranged circularly around a central axis of the reinforcing member and spaced apart from each other in a direction of the central axis, and a plurality of rows of elongated members situated between and connected to adjacent two rows of the joint members.

4. An expandable reinforcing member according to claim 2, wherein said elongated members in each row being inclined substantially in a same direction and diagonally with an acute angle with respect to a line on a surface of the reinforcing member parallel to the central axis of the reinforcing member, said elongated members in two rows sandwiching one row of the joint members and being connected thereto to be arranged substantially symmetrically relative to said one row of the joint members so that when a radial force is applied from an inside of the reinforcing member, the elongated members are pivoted relative to the joint members to thereby allow the reinforcing member to have a second diameter larger than a first diameter.

5. An expandable reinforcing member according to claim 4, wherein said each hollow mesh portion further includes an end section having second elongated members substantially parallel to the central axis of the reinforcing member and connected to the circularly arranged joint members, and end bars, each end bar connecting two adjacent second elongated members.

* * * * *